United States Patent
Fleischer et al.

(10) Patent No.: US 9,523,665 B2
(45) Date of Patent: Dec. 20, 2016

(54) DEVICE AND METHOD FOR DETERMINING CARBON DIOXIDE CONTENT OF AIR

(75) Inventors: Maximillian Fleischer, Hoehenkrichen (DE); Roland Pohle, Herdweg (DE); Stefan Stegmeier, Munich (DE); Oliver Von Sicard, Munich (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 183 days.

(21) Appl. No.: 14/126,351

(22) PCT Filed: May 29, 2012

(86) PCT No.: PCT/EP2012/060001
§ 371 (c)(1),
(2), (4) Date: Dec. 13, 2013

(87) PCT Pub. No.: WO2012/171783
PCT Pub. Date: Dec. 20, 2012

(65) Prior Publication Data
US 2014/0109649 A1 Apr. 24, 2014

(30) Foreign Application Priority Data
Jun. 15, 2011 (DE) .......................... 10 2011 077 559

(51) Int. Cl.
*G01N 33/00* (2006.01)
*G01N 27/414* (2006.01)

(52) U.S. Cl.
CPC ........ *G01N 33/004* (2013.01); *G01N 27/4143* (2013.01)

(58) Field of Classification Search
CPC G01N 33/004; G01N 33/006; G01N 33/0062; G01N 27/002
See application file for complete search history.

(56) References Cited

U.S. PATENT DOCUMENTS 5,521,099 A * 5/1996 Glaunsinger ........ G01N 27/002
422/88
5,635,136 A * 6/1997 Glaunsinger ........ G01N 27/002
422/88

(Continued)

FOREIGN PATENT DOCUMENTS

DE 102009040053 A1 3/2011
DE 102011077559.5 6/2011

(Continued)

OTHER PUBLICATIONS

Stegmeier, Optimization of the work function response of CO2-sensing Polysiloxane layers by modification of the polymerization, IEEE 2009, p. 1742.*

(Continued)

*Primary Examiner* — Daniel S Larkin
*Assistant Examiner* — Jamar Ray
(74) *Attorney, Agent, or Firm* — Slayden Grubert Beard PLLC

(57) ABSTRACT

A gas sensor, for example for use in air conditioning systems, has a gas-sensitive layer that includes a material that is sensitive to carbon dioxide. The material has a cross-sensitivity to air humidity. This is compensated for by measurement at two different temperatures. The measured gas values are calculated together, with the assumption that the sensitivity of the gas sensor to carbon dioxide exhibits a different curve with the temperature of the gas sensor than the sensitivity to water.

13 Claims, 3 Drawing Sheets

(56) References Cited

U.S. PATENT DOCUMENTS

| | | | |
|---|---|---|---|
| 7,058,518 B2* | 6/2006 | Shoji | G01N 27/18 702/24 |
| 8,683,845 B2 | 4/2014 | Fleischer et al. | |
| 2002/0047311 A1* | 4/2002 | Hugh | C12M 23/48 307/116 |
| 2006/0042965 A1 | 3/2006 | Sasaki et al. | |
| 2006/0249401 A1* | 11/2006 | Lehmann | G01N 27/4143 205/775 |
| 2008/0016949 A1* | 1/2008 | Fleischer | G01N 27/4143 73/31.06 |
| 2011/0146382 A1 | 6/2011 | Fleischer et al. | |
| 2012/0171775 A1* | 7/2012 | Vogt | B82Y 15/00 436/151 |

FOREIGN PATENT DOCUMENTS

| | | |
|---|---|---|
| EP | 1 176 418 A2 | 1/2002 |
| EP | 1 510 814 A1 | 3/2005 |
| WO | 97/28441 | 8/1997 |
| WO | 2011/026775 A1 | 3/2011 |

OTHER PUBLICATIONS

International Search Report for PCT/EP2012/060001; mailed Aug. 28, 2012.

S. Stegmeier et al.; "Sensing of $CO_2$ at room temperature using work function readout of (hetero-)polysiloxanes sensing layers"; Sensors and Actuators B: Chemical, vol. 154, 2011, pp. 206-212.

H-E. Endres et al.; A capacitive $CO_2$ sensor system with suppression of the humidity interference; Sensor and Actuators B, vol. 57, 1999, pp. 83-87.

Office Action dated May 12, 2015 in corresponding Chinese Patent Application No. 201280029534.6.

Burgmair et al., "Humidity and temperature compensation in work function gas sensor FETs", Sensors and Actuators, 2003, vol. 93, pp. 271-275.

* cited by examiner

DEVICE AND METHOD FOR DETERMINING CARBON DIOXIDE CONTENT OF AIR

CROSS REFERENCE TO RELATED APPLICATIONS

This application is the U.S. national stage of International Application No. PCT/EP2012/060001, filed May 29, 2012 and claims the benefit thereof. The International Application claims the benefit of German Application No. 102011077559.5 filed on Jun. 15, 2011, both applications are incorporated by reference herein in their entirety.

BACKGROUND

Described below are a carbon dioxide sensor for determining the carbon dioxide content of air and a method for creating a measured gas value which represents the carbon dioxide concentration in air.

The detection of carbon dioxide is of great interest for a number of applications. Examples are the assessment of air quality in internal spaces, energy-efficient control of air conditioning systems or checking cleaned air. The aim of carbon dioxide detection can be to enhance comfort. It is however also possible to achieve significant energy savings under some circumstances.

Thus, for example, in a well insulated building, almost half the energy needed for air conditioning can by saved by demand-driven air conditioning. The demand is oriented inter alia in such systems to the carbon dioxide content of the air. In the automotive field too a demand-driven ventilation and air conditioning of the passenger compartment is advantageous. A figure for reduction in the fuel consumed for air conditioning is estimated at 0.3 l per 100 km.

Under normal environmental conditions carbon dioxide occurs in the air in a concentration or around 380-400 ppm. A sensor for carbon dioxide must be capable, using this basic concentration as its starting point, of detecting increased concentrations of up to 4000 ppm for example. It is problematic in such cases that the carbon dioxide molecule is a linear, symmetrical molecule and therefore no electrical dipole moment is present, which with various transducer principles can give rise to a sensor signal. Furthermore the molecule is chemically very unreactive.

At present very successful methods for determining the concentration of carbon dioxide are therefore to be found primarily in the area of optical spectroscopy. These methods make use of the fact that in specific wavelength ranges, for example at around 4.3 µm wavelength, carbon dioxide absorbs light. This makes possible an exact and selective measurement of the concentration of carbon dioxide. In such cases it is not a matter of the chemical reactivity of the carbon dioxide. The disadvantage of optical spectroscopy is however the complex structure of the measurement systems and the significant outlay necessary for evaluating the measured spectra. This ultimately leads to comparatively large and expensive measurement systems.

Solid-state sensors, such as semiconductor gas sensors for example, avoid the disadvantages of the optical measurement systems. They are small, extremely cheap to manufacture by comparison through mass production and need a less complex signal evaluation. However the disadvantage of solid-state sensors is that they are dependent on a certain reactivity of the molecules to be measured and simultaneously however detect all molecules which just have a certain reactivity. To put it another way, the solid-state sensors have a low selectivity. Above all this makes the measurement of less reactive species such as carbon dioxide difficult with such sensors, since they mostly react very strongly to hydrocarbons or ozone.

The number of potential interference gases is substantial in such cases. It includes nitrogen dioxide ($NO_2$), carbon monoxide (CO) and hydrogen ($H_2$), ammonia ($NH_3$), ethanol or hydrochloric acid (HCl), nitrogen monoxide (NO), sulfur oxide ($SO_x$), carbonyl sulfide (COS), laughing gas ($N_2O$) and prussic acid (HCN), water ($H_2O$) as well as organic gases such as methane, ethane, ethene, acetylene and other hydrocarbons such as formaldehyde ($CH_2O$). Other interference gases are amines ($NH_2R_1$, $NH_1R_2$, $NR_3$), amides ($RC(O)NH_2$, $RC(O)NHR'$, $RC(O)NR'R$), acrolein ($C_3H_4O$) and phosgene ($COCl_2$), aromatics such as benzol ($C_6H_6$), ethyl benzol, chlorbenzol, toluol, xylol, styrol and phenol ($C_6H_6O$). There is also ozone ($O_3$), the large group of VOCs (volatile organic compounds).

Some of these gases already occur in normal ambient air, for example ozone. Further sources for gases are fires, cigarette smoke, human activity, the use of chemical media such as cleaning agents, foodstuffs left open or technical devices such as printers. Road traffic and even the weather conditions also lead to the occurrence of gases.

The publication by H.-E. Endres et al., "A capacitive $CO_2$ sensor system with suppression of the humidity interference", Sensors and Actuators Vol. 57 (1999), 83-87 discloses a $CO_2$ sensor which is based on the principle of capacitance measurement. With the disclosed capacitive sensor an additional humidity sensor is used in order to generate a humidity signal.

A potential-controlled humidity sensor which is able to be used for this purpose is known for example from EP 1 176 418 A2. The potential-controlled humidity sensor has a gas-sensitive area which is able to be polarized independently of a humidity. Furthermore the gas sensitive area exhibits a relative dielectricity constant, which is dependent on the humidity.

The disadvantage of the known sensors is that a further sensor is necessary to determine and compensate for air humidity. Just like the actual carbon dioxide sensor, this must be calibrated and evaluated and must also fulfill the characteristics required for the carbon dioxide sensor, for example longevity.

SUMMARY

Described below are a gas sensor which makes it possible to detect carbon dioxide and a method for generating a measured gas value which represents the carbon dioxide concentration in air. In this case the influence of environmental variables on the measurement signal should especially be compensated for in an adequate manner.

The device for determining the carbon dioxide content of air has at least one carbon dioxide-sensitive gas sensor for outputting a measured gas value. Furthermore it has an apparatus for temperature control of the gas sensor. Furthermore an apparatus for evaluating the measured gas value for determining the carbon dioxide content of the air is provided.

The device is embodied such that the apparatus for temperature control sets at least two different temperatures during the operation of the gas sensor and at least one measured gas value is recorded at each of the two different temperatures.

Furthermore the device is embodied such that the apparatus for evaluation determines the carbon dioxide content at the different temperatures from the measured gas values while correcting the influence of the air humidity, in that the apparatus for evaluating the measured gas values calculates the values together, with the assumption that the sensitivity of the gas sensor to carbon dioxide exhibits a different curve with the temperature of the gas sensor than the sensitivity to water.

The gas sensor in this case features a gas-sensitive material, for example in the form of a gas-sensitive layer. The gas-sensitive material is designed so that it responds to carbon dioxide. In other words the measured gas value changes for a change in the concentration of carbon dioxide in the surrounding air. It is expedient in this case for this change to be measurable at a concentration change of especially 50 ppm $CO_2$, i.e. for the change to be greater than the signal noise. In another example it is also sufficient for the change in the measured gas value to be able to be measured at a change in concentration of 500 ppm $CO_2$.

This is referred to as the concentration of carbon dioxide or water in the air. This is also understood as the usual type of measurement of most gas-sensitive materials, in which the absolute presence of the gas, i.e. the partial pressure of the gas, is measured rather than a relative portion of the gas. The measured gas value thus expediently depends on the partial pressure of carbon dioxide and water.

Overall the device is advantageously designed so that the calculation of the measured gas values leads to the influence of a change in air humidity on the measured gas value being reduced. In this case the temperature control of the gas sensor solely enables a correction of the measured gas value to be made possible. In other words, an additional humidity sensor, with all its associated disadvantages, is not necessary.

An particular advantage is that the sensor is also heated up at the same time as the opportunity of correcting the measured gas value. I.e. molecules which at room temperature would have remained adsorbed on the gas-sensitive layer for example are removed by the intermittent operation at increased temperature, through which the baseline of the gas sensor signal overall is stabilized.

In accordance with an advantageous embodiment, the measured gas value for the gas sensor is generated by an evaluation of the work function of the material.

In accordance with a further advantageous embodiment, the gas-sensitive material has primary amino groups (R—$NH_2$, R=residue, e.g. alkyl residue). These primary amino groups, at room temperature in the presence of $CO_2$, form reversibly-charged species (e.g. bicarbonate and carbamate), which lead to a marked change in the work function. Materials with primary amino groups exhibit a marked reversible reaction to changes of the partial pressure of carbon dioxide. At the same time it has been shown that the cross sensitivities in relation to certain interference gases such as $NO_2$, volatile hydrocarbons or solvents for example, are not large.

But it has surprisingly transpired above all in measurements that $CO_2$ sensors, based on work function measurement at the material with primary amino groups, under some circumstances respond to air humidity, and do so more strongly than to the many other interference gases. This was already unexpected because, with many of the usual layer materials used for work function measurement, although cross sensitivities occur, they hardly ever occur for water. Examples are copper phtalocyanine (CuPC), lead phtalocyanine (PbPC) or other phtalocyanines, gallium oxide ($Ga_2O_3$), platinum (Pt) and titanium nitride (TiN).

For interference gases which trigger a change of work function with primary amino groups there would again be more candidates. The air namely contains gases in variable concentration which react strongly with primary amines (. . . —$NH_2$), such as especially nitrogen dioxide ($NO_2$), alcohols (R—OH), nitrogen monoxide (NO), ozone ($O_3$), hydrogen ($H_2$), carbon monoxide (CO), ammonia ($NH_3$), hydrochloric acid (HCl), nitric acid (HCN), sulfur oxide ($SO_x$), carbonyl sulfide (COS), laughing gas ($N_2O$) and organic gases.

In such cases the influence of water does not show up uniquely more clearly than the influence of other sources on the measurement result. Similarly and not immediately differently the measurement result changes as a consequence of temperature changes, contamination and also incompletenesses in the signal evaluation, zero point drift and hysteresis effects, i.e. prior stresses from preceding series of measurements. Therefore the surprisingly established effect of the air humidity even remained undiscovered during a series of measurements.

In the method for determining the carbon dioxide content of air by a carbon dioxide-sensitive gas sensor while correcting the influence of the air humidity, the gas sensor is bought during operation to at least two different temperatures, at least one measured gas value is recorded at each of the two different temperatures and the carbon dioxide content is determined from the measured gas values at the different temperatures while correcting the influence of the air humidity by the measured gas values being calculated together, with the assumption that the sensitivity of the gas sensor to carbon dioxide exhibits a different curve with the temperature of the gas sensor than the sensitivity to water.

Thus the measured gas value is corrected so that the influence of the air humidity on the carbon dioxide measurement is at least reduced.

It is especially advantageous for the reaction of the measured gas value to a change in the relative air humidity by 10% to have at least 5%, especially at least 10%, or in another example at least 20% of the strength of the reaction to a change in concentration of carbon dioxide by 1000 ppm.

A field effect transistor structure is especially advantageous as the structure for the gas sensor. The basic field effect transistor structure is known from electronic components, i.e. drain and source electrodes and a conductive channel adjacent to a gate electrode exist. The special aspect of the gas sensor with field effect transistor structure is that the gas-sensitive material is provided adjacent to the conductive channel. This means that electrical changes in the gas-sensitive material influence the conductivity in the channel.

The functioning of gas sensors on the basis of work function changes or contact potential measurements, such as for example by a gas-sensitive field effect transistor, is based on the physical fact that adsorbed gas molecules on the material surface are either present as permanent dipoles or induce dipoles. The work function of the material covered with gas then changes by the potential jump at the dipole layer on the surface. This potential jump can couple into the gate voltage of a field effect transistor, wherein the change in the starting voltage at constant current can then be used as the measured value.

Such a field effect transistor structure can be realized by the gas-sensitive material being applied directly to the gate electrode. In this case the manufacturing of the sensor in large volumes is possible in micromechanical fabrication. In such cases it can be advantageous for the gas-sensitive material to either be made very thin or even designed to let gas through in order to obtain an electrical effect of the gas reactions on the conductive channel that is as great as possible.

Especially advantageously the GasFET is equipped with an air gap between the sensitive layer and the conductive channel of the field effect transistor structure. The realization of a gas field effect transistor (GasFET), in which a small air gap (0.5-5 μm) is present between gate electrode and channel area of the transistor, makes provision for the side of the gate electrode facing towards the air gap to be provided with the gas-sensitive material, for example coated with it. The gas-induced change in the electron work function causes an additional potential in the order of magnitude of typically 10-100 mV to occur on the sensitive layer, which acts as an additional gate voltage on the transistor.

An especially advantageous structure provides for a GasFET, especially a hybrid GasFET with a gas-sensitive layer with primary amino groups. It is also advantageous for the gas-sensitive material to feature a polymer. The strength of the cross-sensitivity to an air humidity of polymer-based gas-sensitive layers depends on the type of readout of the signal. Precisely during the transition from known capacitive sensors to read out by the work function, especially by a GasFET, as well as the surprising and significant advantage of measurement at room temperature, changed cross sensitivities also emerged. Thus the sensitivity to air humidity is surprisingly strong during a readout by work function as is performed with GasFETs.

In an especially advantageous embodiment and development, the device is embodied such that one of the different temperatures is a temperature at which the gas-sensitive material no longer reacts to carbon dioxide. In other words a temperature other than one of the two different temperatures is selected at which the sensitivity of the gas sensor to carbon dioxide at least largely disappears. The correction of the measured gas value is then advantageously especially simple since the measured gas value at this temperature practically only corresponds to a humidity measurement.

To enable influences of pressure to be compensated for, provision is made in a further embodiment for a pressure sensor. The air pressure can vary for example because of height above sea level and weather influences. It is especially advantageous for the pressure sensor to be realized monolithically with the gas sensor and/or the further sensors present, i.e. created on a common substrate.

The influence of the air humidity on the measured gas value can be divided into 2 effects. The first effect corresponds to the function that gas-sensitive material could have as a humidity sensor. It is entirely independent of the presence of carbon dioxide.

The second effect is the size of the measurement effect on $CO_2$ being somewhat dependent on the air humidity obtaining in each case, i.e. that the signal caused for example by a change in concentration of 100 ppm carbon dioxide is dependent on partial water pressure. Thus a change in concentration of 100 ppm carbon dioxide at an air humidity of 30% can for example create a change in the electrical signal of 10 mV while the same change in concentration at 70% air humidity creates a change in the electrical signal of 13 mV. In this case the difference of 40% air humidity, which itself for example creates a signal change of 40 mV, is already taken into account and corrected. I.e. even if the first effect, which is explained further above, is completely corrected, the second effect remains and can likewise be corrected in order to increase the accuracy of the carbon dioxide measurement.

In an advantageous embodiment, the first effect is corrected. It is especially advantageous for the accuracy of the measurement for the second effect to be corrected in addition. In this case not only the discrepancy of the measured gas value caused by humidity is calculated out but in addition the remaining measured gas value, which then stems from the carbon dioxide, is corrected on the basis of the humidity.

For this purpose the air humidity can also be determined from the measured gas values at the different temperatures. Then for example, on the basis of correction values present in tabular form the measured gas value can be corrected. It is also possible to perform the correction analytically with stored coefficients.

In an advantageous embodiment, the device is designed so that the delay at the higher of the different temperatures corresponds to at least half the delay at the lower of the different temperatures. In other words the gas sensor will only be operated for a shorter time at increased temperature by comparison with operation at room temperature for example. Energy is advantageously saved by this. In particular the dwell time at the higher of the different temperatures can only amount to a tenth of the dwell time at the lower of the different temperatures.

In an advantageous embodiment, the device is embodied to perform the setting of the different temperatures continuously, especially in that temperature ramps or sinusoidal temperature curves are used. For example the temperature can thus be changed in continuous triangular or sawtooth ramps.

In such cases it is advantageous if, in addition to the described evaluation of the measured gas values at the different temperatures, there is an evaluation of the time curve of the signals, for example with multivariate methods such as the PLS.

BRIEF DESCRIPTION OF THE DRAWINGS

These and other aspects and advantages will become more apparent and more readily appreciated from the following description of the exemplary embodiments, taken in conjunction with the accompanying drawings of which.

DETAILED DESCRIPTION OF THE PREFERRED EMBODIMENT

Figure 1:
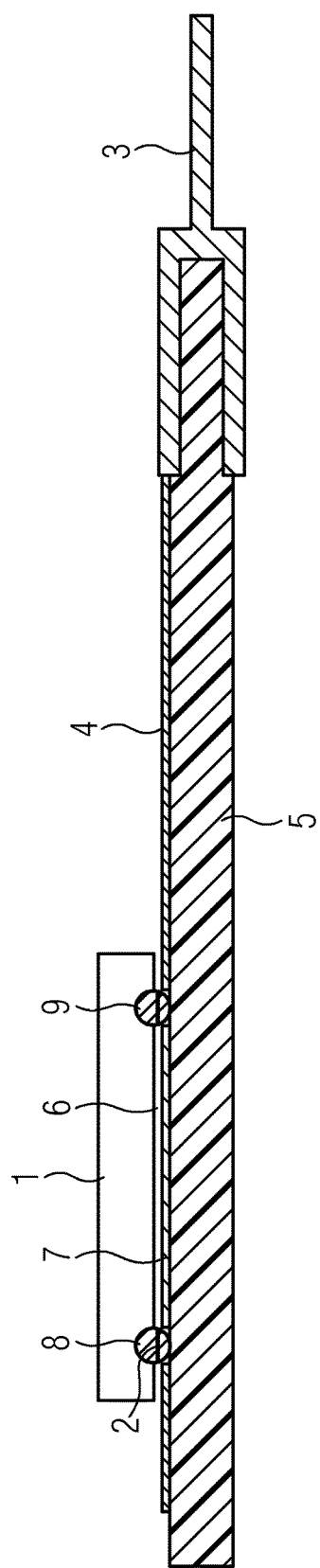
FIG. 1 is a cross section of a structure for a carbon dioxide sensor as SGFET.

Reference will now be made in detail to the preferred embodiments, examples of which are illustrated in the accompanying drawings, wherein like reference numerals refer to like elements throughout.

FIG. 1 shows the basic structure of a gas-sensitive FET in accordance with an example of a structure. Illustrated in FIG. 1 is a CMOS transistor 1 with a source electrode 8 and a drain electrode 9. In this case a FET structure in the form of the CMOS transistor 1 is mounted in flip-chip technology on a ceramic substrate 5 provided with conductor tracks 4. This can be done for example by a conductive adhesive 2. The gas-sensitive layer 7 is partly applied to the ceramic substrate 5 and is contacted accordingly with the conductor tracks 4. The gas channel is the air gap 6 between gate and CMOS transistor. The ceramic substrate 5 serves as a carrier of the gas-sensitive layer and simultaneously as a carrier of the entire sensor structure, so that in this example no building into a sensor base is necessary. Plug-in pins 3 can be attached to this ceramic substrate 5, so that the electronic component can be inserted directly for example into a single in-line plug connection. As an alternative other designs are also possible, for example design as an SMD (Surface Mounted Device) component.

Figure 2:
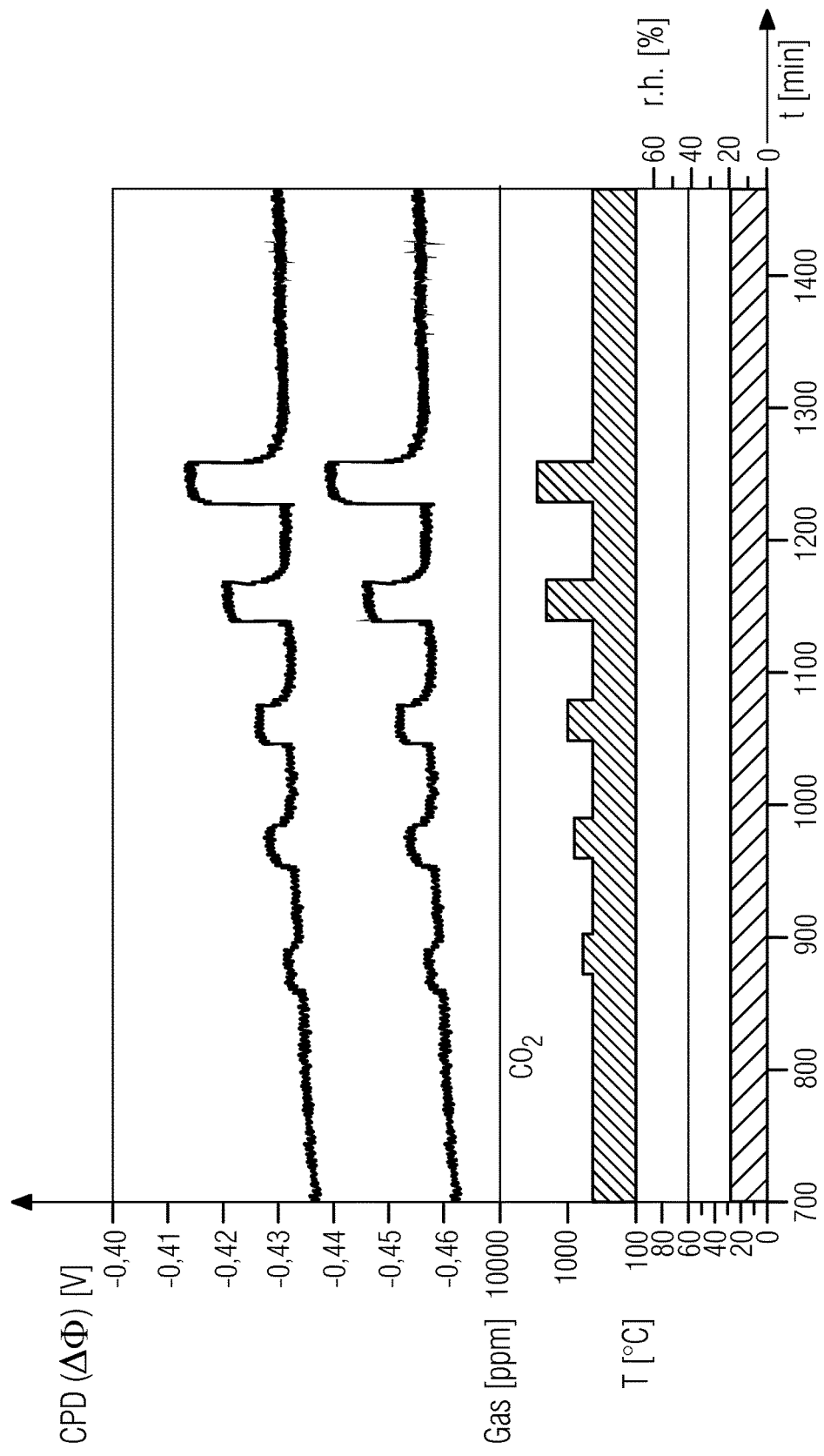
FIG. 2 is a graph of a measurement result of an AMO/PTMS layer for carbon dioxide.

A first sensor, of which the measurement result is shown in FIG. 2, has a so-called AMO/PTMS layer as its sensor layer. This material system is also referred to as hetero polysiloxane, since here the material is formed from two different base silanes. To manufacture this layer aminopropyltrimethoxysilane (AMO) and propyltrimethoxysilane (PTMS) are dissolved in methanol. The solution is cooked in a glass vessel with the addition of a small amount of water for 3 hours under reflux. The solution produced is applied after cooling by a spin-coating process to a substrate (e.g. gold-coated $Al_2O_3$ ceramic) and hardened in an oven in a nitrogen atmosphere for sixteen hours at 120° C. The layer thus created has a thickness of 12.8 µm in this example.

FIG. 2 shows two measurement results on the sensor layer thus obtained taken by a Kelvin probe. During the period of the measurement, the first sensor was operated at room temperature, i.e. without heating. The artificially created gas environment of the sensor layer has a relative humidity of 40%. During the several hours of measurement the concentration of carbon dioxide was increased in stages from a basic level of approximately 400 ppm at intervals and reset again to the basic level. The smallest increased concentration created lay at appr. 600 ppm, i.e. appr. 200 ppm above the basic level. The highest concentration created lay in this case at appr. 4000 ppm. The measurement signal CPD (Contact Potential Difference) shows a clear peak at a concentration of 4000 ppm $CO_2$. At lower concentration increases the signal is correspondingly weaker. Even at the lowest concentration increase of appr. 200 ppm the signal is clearly recognizable.

Figure 3:
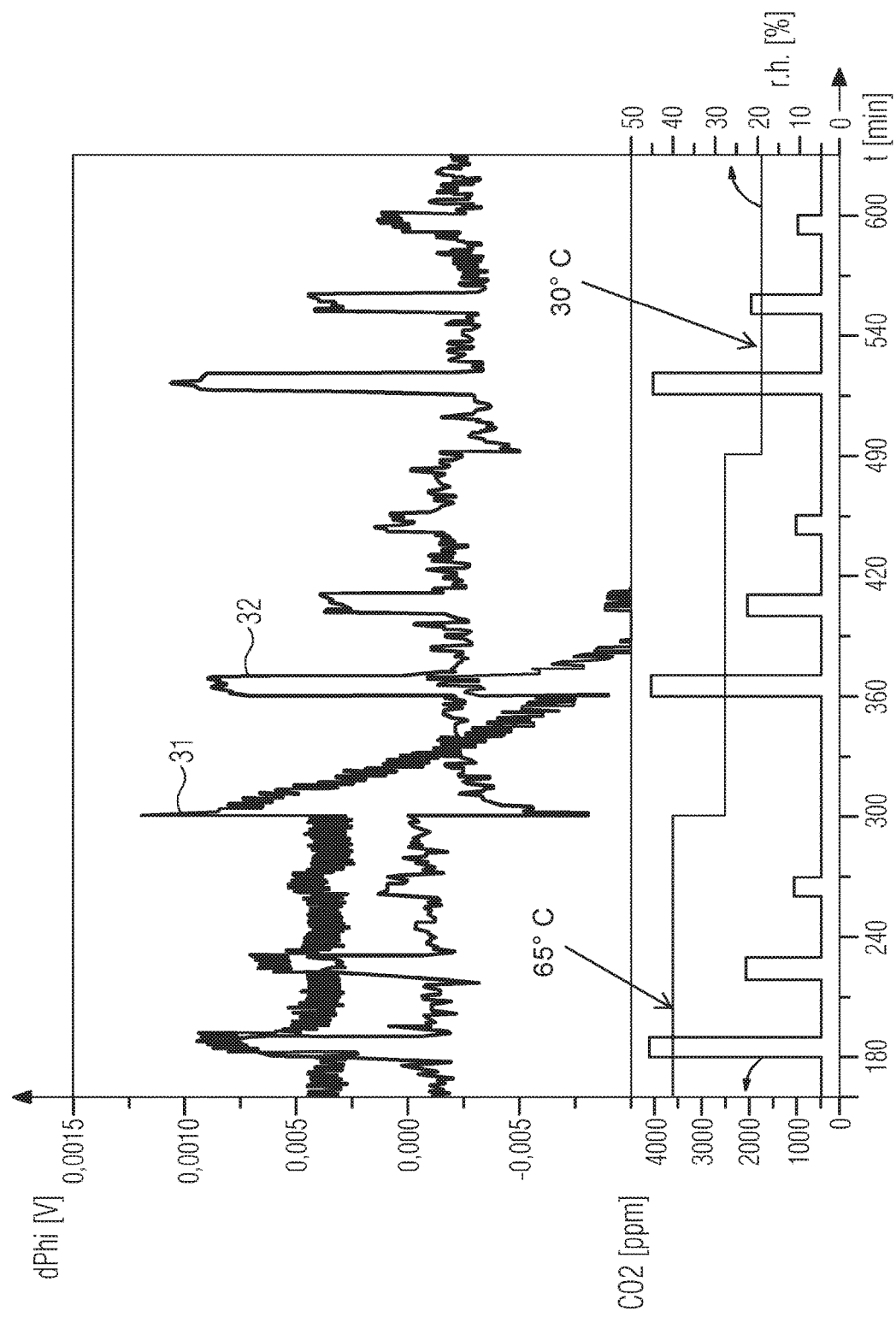
FIG. 3 is a graph of a measurement result of an AMO/PTMS layer for $CO_2$ and water.

FIG. 3 shows two measurement results on an AMO sensor layer. The structure of sensor is shown in FIG. 1. The artificially created gas environment of the sensor layer was controlled so that both the humidity (lines associated with right-side ordinate) and also the carbon dioxide concentration (lines associated with left-side ordinate) were varied. A first measurement result 31 in this case shows the curve of the sensor signal without temperature variation. It can be seen that the sensor layer shows marked reactions to changes in humidity, especially a signal drift when the air humidity changes.

A second measurement result 32 shows the curve of the corrected sensor signal, wherein a measurement was carried out at different temperatures. It can be seen that the signal drift is markedly reduced when the humidity changes, i.e. the influence of the humidity is markedly reduced. With the sensor used by way of example a temperature of 65° C. was chosen as the higher temperature. With the actual sensor that was used, the sensitivity to carbon dioxide disappears almost entirely at this temperature. The lower temperature was 30° C. Since the sensitivity to carbon dioxide 65° C. was negligible, the following formula emerges as the correction formula for the measured carbon dioxide value dPhi:

30° C.: $d\text{Phi}=L([H_2O], [CO_2])$

65° C.: $d\text{Phi}=L([H_2O])$

->$d\text{Phi}(30° C.)-A*d\text{Phi}(65° C.)=L([CO_2])$

In this formula L( ) designates a linear function and A is a factor to be determined.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide* v. *DIRECTV,* 358 F3d 870, 69 USPQ2d 1865 (Fed. Cir. 2004).

The invention claimed is:

1. A device for determining carbon dioxide content of air, comprising:
    at least one carbon dioxide-sensitive gas sensor outputting of a measured gas value;
    a temperature control apparatus automatically setting at least two different temperatures during operation of the at least one carbon dioxide-sensitive gas sensor; and
    an evaluation apparatus recording at least one measured gas value for each of the at least two different temperatures and evaluating measured gas values to determine the carbon dioxide content of the air at the at least two different temperatures while correcting influence of air humidity by correlating the measured gas values using a first curve representing sensitivity of the at least one carbon dioxide-sensitive gas sensor to carbon dioxide and a second curve representing sensitivity of the at least one carbon dioxide-sensitive gas sensor to water at the at least two different temperatures.

2. The device as claimed in claim 1, wherein the at least one carbon dioxide-sensitive gas sensor includes a gas-sensitive material having primary amino groups.

3. The device as claimed in claim 2, wherein the at least one carbon dioxide-sensitive gas sensor determines the measured gas value by evaluating a work function of the gas-sensitive material.

4. The device as claimed in claim 3, wherein the gas-sensitive material includes a polymer.

5. The device as claimed in claim 4, wherein one of the at least two different temperatures is a temperature at which the gas-sensitive material does not react to carbon dioxide.

6. The device as claimed in claim 5, wherein the at least one carbon dioxide-sensitive gas sensor includes a field effect transistor structure with an air gap between the gas-sensitive material and a conductive channel of the field effect transistor structure.

7. The device as claimed in claim 6, further comprising a pressure sensor.

8. The device as claimed in claim 7, wherein the gas sensitive material results in a reaction of the measured gas value to a change in concentration of the relative humidity by 10% having at least 5% of strength of the reaction to a change in concentration of carbon dioxide by 1000 ppm.

9. The device as claimed in claim 8, further comprising means for correcting the measured gas value of the at least one carbon dioxide-sensitive gas sensor, such that the influence of the air humidity on the influence of carbon dioxide on the measured gas value is corrected.

10. The device as claimed in claim 9, wherein the device calculates to check whether change over time of the measured gas value of the at least one carbon dioxide-sensitive gas sensor and/or of the measured humidity value exceeds a definable threshold value, taking into consideration the measured gas value only after a definable waiting time has elapsed.

11. The device as claimed in claim 10, wherein a dwell time at a highest of the at least two different temperatures corresponds to at least half the dwell time at a lowest of the different temperatures.

12. The device as claimed in claim 11, wherein the temperature control apparatus sets the different temperatures continuously using one of temperature ramps and sinosoidal temperature curves.

13. A method for determining carbon dioxide content of air using a carbon dioxide-sensitive gas sensor while correcting for influence of air humidity, comprising:
- automatically operating the carbon dioxide-sensitive gas sensor at least two different temperatures;
- recording at least one measured gas value at each of the at least two different temperatures; and
- determining the carbon dioxide content of the air at the at least two different temperatures while correcting the influence of the air humidity, by correlating the measured gas values using a first curve representing sensitivity of the carbon dioxide-sensitive gas sensor to carbon dioxide and a second curve representing sensitivity of the carbon dioxide-sensitive gas sensor to water at the at least two different temperatures.

* * * * *